United States Patent [19]
Grooters et al.

[11] Patent Number: 5,876,383
[45] Date of Patent: Mar. 2, 1999

[54] CANNULA

[76] Inventors: Robert K. Grooters, 5535 Glen Oaks Pt., West Des Moines, Iowa 50266-6627; Robert J. Todd, 3415 S. Eastwood Dr., Salt Lake City, Utah 84109

[21] Appl. No.: 940,745

[22] Filed: Sep. 30, 1997

[51] Int. Cl.⁶ .................................................. A61M 25/00
[52] U.S. Cl. ........................................ 604/264; 604/280
[58] Field of Search .................................. 604/264, 280, 604/239, 54, 49, 53

[56] References Cited

U.S. PATENT DOCUMENTS

| | | |
|---|---|---|
| 191,879 | 6/1877 | Pfarre . |
| 1,998,225 | 4/1935 | Dow ........................................ 604/280 |
| 3,828,767 | 8/1974 | Spiroff . |
| 4,198,984 | 4/1980 | Taylor ..................................... 128/349 |
| 4,276,880 | 7/1981 | Malmin ................................... 128/221 |
| 4,361,152 | 11/1982 | Patel ........................................ 604/99 |
| 4,368,738 | 1/1983 | Tersteegen et al. . |
| 4,617,019 | 10/1986 | Fecht et al. . |
| 4,643,712 | 2/1987 | Kulik et al. ................................ 604/4 |
| 4,795,446 | 1/1989 | Fecht ...................................... 604/264 |
| 4,863,441 | 9/1989 | Lindsay et al. ......................... 604/280 |
| 5,044,369 | 9/1991 | Sahota ................................... 604/280 |
| 5,084,033 | 1/1992 | O'Neill et al. . |
| 5,147,334 | 9/1992 | Moss ...................................... 604/264 |
| 5,167,645 | 12/1992 | Castillo . |
| 5,259,371 | 11/1993 | Tonrey ............................... 128/200.26 |
| 5,290,267 | 3/1994 | Zimmermann . |
| 5,320,599 | 6/1994 | Griep et al. ............................... 604/35 |
| 5,344,412 | 9/1994 | Wendell et al. ........................ 604/280 |
| 5,354,288 | 10/1994 | Cosgrove et al. ...................... 604/264 |
| 5,360,414 | 11/1994 | Yarger .................................... 604/264 |
| 5,364,373 | 11/1994 | Waskonig et al. .................. 604/239 X |
| 5,389,074 | 2/1995 | Parker et al. ......................... 604/54 X |
| 5,407,441 | 4/1995 | Greenbaum ............................ 604/280 |
| 5,451,216 | 9/1995 | Quinn ..................................... 604/270 |
| 5,546,675 | 8/1996 | Wolbring et al. . |
| 5,599,322 | 2/1997 | Quinn ................................. 604/280 X |
| 5,616,137 | 4/1997 | Lindsay .................................. 604/264 |
| 5,643,226 | 7/1997 | Cosgrve et al. . |
| 5,685,865 | 11/1997 | Cosgrove et al. . |
| 5,749,889 | 5/1998 | Bacich et al. . |

FOREIGN PATENT DOCUMENTS

| | | |
|---|---|---|
| 0092927 B1 | 8/1986 | European Pat. Off. . |
| 0159773 B1 | 6/1988 | European Pat. Off. . |
| 0705617 A1 | 4/1994 | European Pat. Off. . |
| 0612536 A1 | 8/1994 | European Pat. Off. . |
| WO 96/18428 | 6/1996 | WIPO . |

*Primary Examiner*—John D. Yasko
*Attorney, Agent, or Firm*—Zarley, McKee, Thomte, Voorhees & Sease

[57] ABSTRACT

An improved aortic cannula is provided for use in heart bypass surgery. The cannula includes an elongated tube with a terminal end. The terminal end has a ramped surface leading to the discharge opening, with a lip extending approximately 70°–90° to the longitudinal axis of the cannula at the bottom of the discharge opening. The curved surface and lip cause the blood to exit the cannula opening in a direction approximately 70°–90° from the longitudinal axis of the cannula, and in a direction toward the ascending aorta. With the improved cannula of the present invention, no blood is directed towards the aortic arch, thereby minimizing the risk of stroke from dislodged plaque commonly found in the aortic arch. The curved surface of the terminal end also reduces the blood flow turbulence, thereby decreasing pressure requirements. The width of the opening allows blood to be discharged in a broadcast band with a radius of approximately 90°.

25 Claims, 2 Drawing Sheets

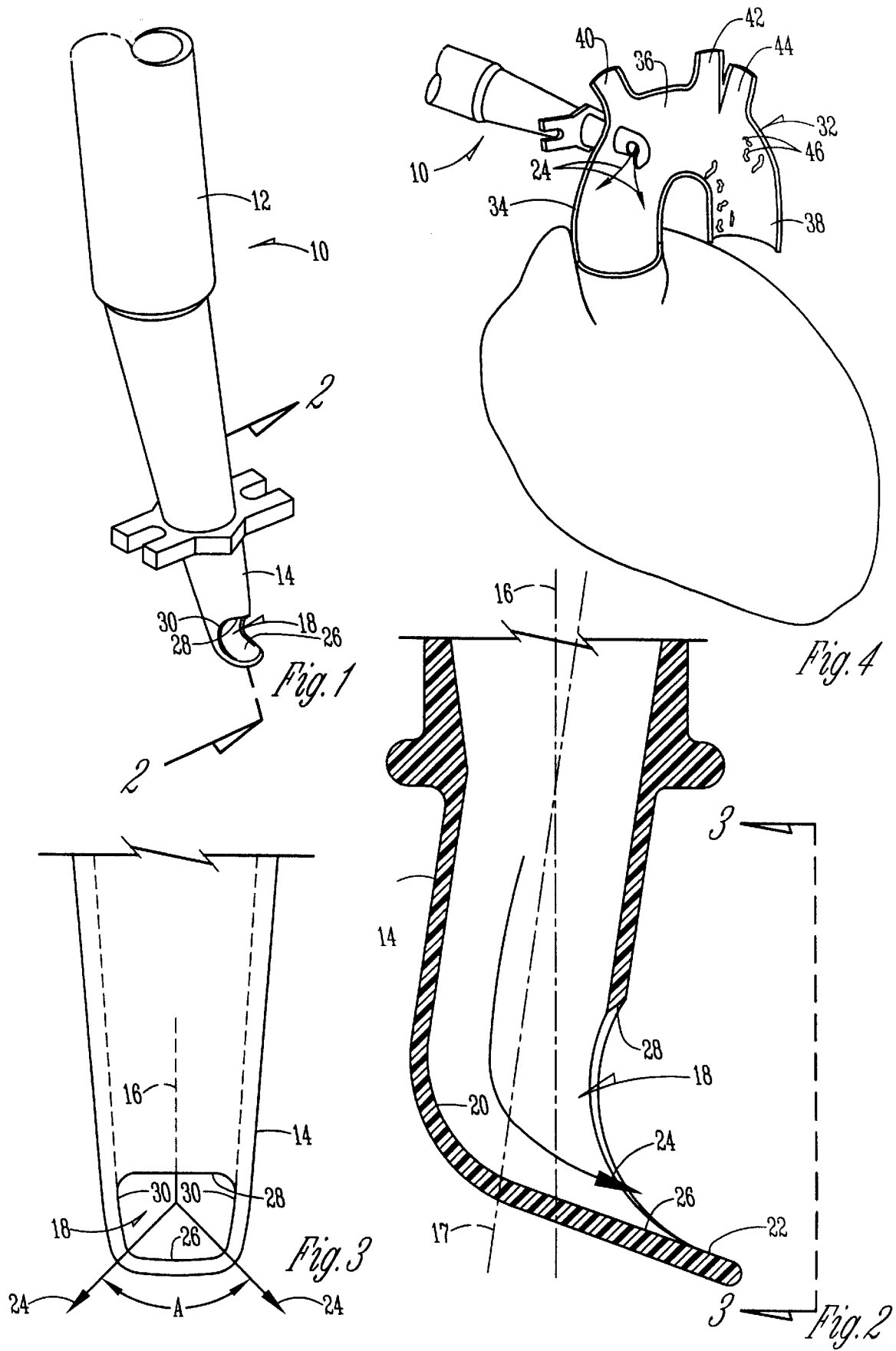

CANNULA

BACKGROUND OF THE INVENTION

The present invention relates generally to medical devices and, in particular, aortic cannulas. Aortic cannulas are used to return blood to the aorta while the heart is by-passed during heart surgery. These cannulas are purposely made with small diameters to minimize the disruption to the aorta, which in many heart surgery patients have advanced complex atherosclerotic plaque with adherent blood thrombi.

Aortic cannulas generally comprise an elongated tube having a terminal end. In at least some styles of conventional cannulas, a single opening is provided in the terminal end which provides a single stream of blood exiting the cannula and entering the aortic arch. Due to the small diameter of the cannula, the flow velocity of the blood through the single opening in the terminal end of the cannula is extremely high, resulting in "jet" flow. The fluid pressure at the discharge end of the prior art cannula is also high. It is believed that the force of this jet stream of blood dislodges atherosclerotic plaque and/or adherent thrombi from the walls of the aorta, causing embolisms and strokes.

Attempts in the art to prevent embolisms resulting from cannulation have included designing the cannula in order to reduce the velocity of blood exiting the terminal end. For instance, U.S. Pat. No. 5,354,288 describes a cannula having a conical diffuser placed toward the proximal end of the cannula. The cannula includes several outlet openings in the sidewall to permit blood deflected by the diffuser to flow out of the cannula. This cannula design, however, still directs blood toward the sides of the aortic arch wherein the atherosclerotic plaque usually lies. Thus, the patient is still susceptible to embolisms and strokes.

Therefore, a primary objective of the present invention is the provision of an improved aortic cannula which does not cause injury to the aortic tissues or dislodge atherosclerotic plaque during cannulation.

Another objective of the present invention is the provision of an improved aortic cannula which directs blood flow from the cannula toward the ascending aorta.

A further objective of the present invention is the provision of an improved aortic cannula which reduces the risk of embolisms or stroke present with the use of conventional cannulas.

Still a further objective of the present invention is the provision of an improved aortic cannula which decreases the jet effect of blood flow from the cannula.

Another objective of the present invention is the provision of an improved cannula which directs the blood flow approximately 90° from the cannula axis and which broadcasts the blood flow through the cannula opening across a radius of approximately 90°.

Yet another objective of the present invention is the provision of an improved aortic cannula which is economical to manufacture and convenient, durable, and safe to use.

These and other objectives will be apparent from the following description of the invention.

SUMMARY OF THE INVENTION

The improved aortic cannula of the present invention includes an elongated tube having a terminal end. The tube internal curved surface leading to an enlarged opening adjacent the terminal end of the cannula. The curved surface terminates in a lip extending beyond the perimeter of the tubular cannula. The curved or ramped surface, in conjunction with the extending lip, directs the blood flow out of the cannula opening at an angle approximately 70°–90° from the longitudinal axis of the cannula. The opening at the terminal end reduces the velocity of the exiting blood. The width of the opening and the lip also broadcasts the exiting blood in a radius of approximately 90°. Preferably, the blood is directed toward the ascending aorta and away from the aortic arch, which often contains atherosclerotic plaque, so that the risk of stroke from dislodged plaque is significantly reduced.

DESCRIPTION OF THE DRAWINGS

FIG. 1 is a perspective view of the improved aortic cannula of the present invention.

FIG. 2 is a section view of the terminal end of the aortic cannula shown along lines 2—2 of FIG. 1.

FIG. 3 is an elevation view of the aortic cannula taken along lines 3—3 of FIG. 2.

FIG. 4 is a schematic diagram of the heart and its primary blood vessels with reference to the aortic cannula of the present invention.

DETAILED DESCRIPTION OF THE PREFERRED EMBODIMENT

Figure 5:
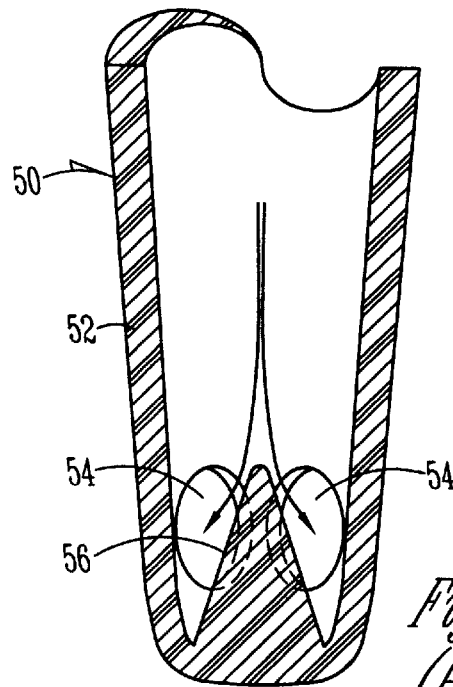
FIG. 5 is a sectional view of a prior art aortic cannula.

The improved aorta cannula of the present invention is generally designated by the reference numeral 10 in the drawings. The cannula 10 comprises an elongated tube 12 with a terminal end 14. As best seen in FIG. 2, the terminal end 14 is angled or tilted slightly with respect to the longitudinal axis 16 of the tube 12. Preferably, the relative angle between the axis 17 of the terminal end 14 and the longitudinal axis 16 of the tube 12 is approximately 8° to 18°. The tube 12 tapers toward the terminal end 14.

An enlarged opening 18 is provided in the terminal end 14. A curved or ramped surface 20 directs blood along a lip 22 extending approximately 70°–90° from the longitudinal axis 16 of the tube 12. The lip 22 extends beyond the perimeter of the tube 12, as best seen in FIG. 2. The opening 18, ramp surface 20 and lip 22 allows the blood to be forced through the cannula 10 at a lower pressure. The large opening also reduces the velocity of the exiting blood. The ramped surface 20 and the lip 22 direct the blood toward the ascending aorta, as indicated by arrow 24, at an angle substantially 70°–90° from the longitudinal axis 16 of the tube 12. Without the extended lip 22, which in effect extends the lower edge 26 of the opening 18 beyond the top edge 28 of the opening, the ramped surface 20 alone will only direct the exiting blood at an angle approximately 45° from the longitudinal axis 16 of the tube 12. The width of the opening 18 also controls the width of the broadcast of the exiting blood. The opening 18 extends approximately 180° from one side 30 to the other side 30, thereby allowing a broadcast of exiting blood with a radius of approximately 90°, as indicated by angle A in FIG. 3. The large size of the opening 18 also decreases the velocity of the blood exiting from the cannula 10.

In FIG. 4, the aorta is designated by the reference numeral 32. The aorta 32 includes three main sections, the ascending aorta 34, the transverse aortic arch 36, and the descending aorta 38. The aortic arch 36 is the primary area where atherosclerotic plaque 46 is found in patients needing heart bypass surgery. Branching from the aorta 32 are three large arteries, the innominate artery 40, the left carotid 42, and the left subclavian 44.

Figure 6:
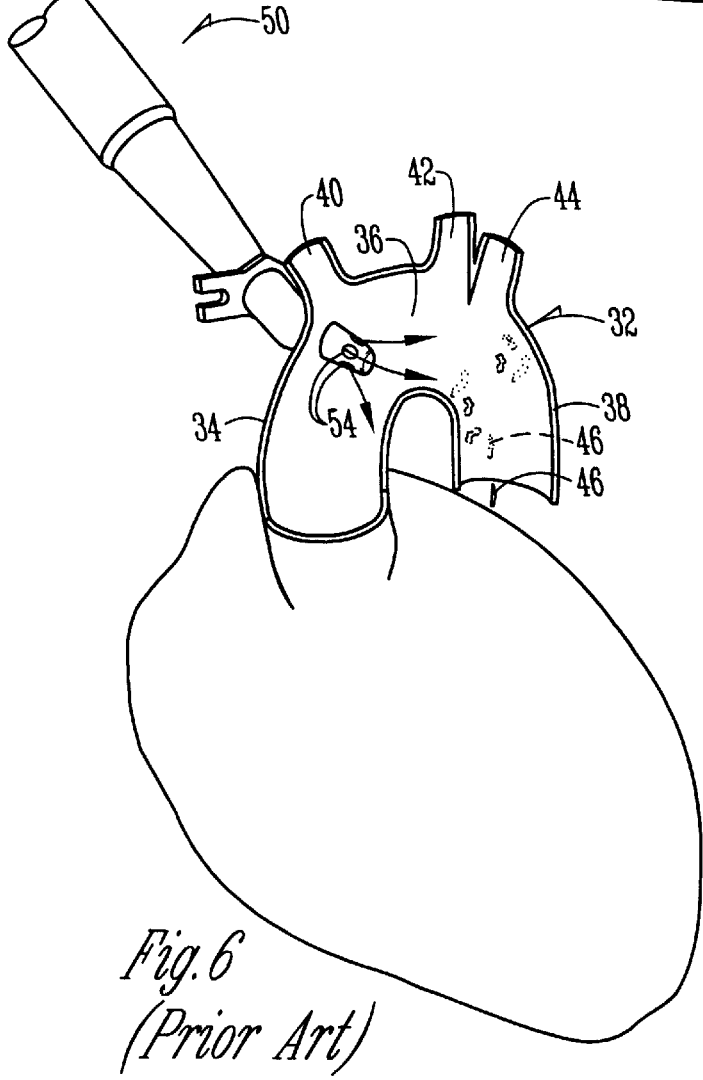
FIG. 6 is a schematic diagram of the heart and its primary blood vessels with reference to a prior art aortic cannula.

A prior art cannula 50 is shown in FIGS. 5 and 6. The terminal end 52 of the prior art cannula 50 has four equally radially spaced openings or slots 54. An inverted cone 56 resides within the terminal end 52 adjacent the openings 54 to disperse blood into four streams directed in all directions from the cannula 50. Thus, a substantial portion of the blood is directed towards the aortic arch, which often has atherosclerotic plaque 46 that can be dislodged by the blood from the cannula 50. In the present invention, the blood flow from the cannula 10 is preferably directed toward the ascending aorta, and away from the aortic arch and atherosclerotic plaque. Even if the blood flow is directed at the aortic arch, the low pressure, low velocity, broad band flow minimizes the risk of dislodging plaque from the artery wall.

Thus, the aortic cannula 10 of the present invention reduces the chance that the plaque 46 will become dislodged during cardiac bypass surgery, and thus, helps to reduce the risk of embolism and strokes. In comparison, with the prior art cannula 50, the blood directed towards the aortic arch 36 may dislodge plaque 46, which then can enter the blood stream and cause a stroke.

Whereas the invention has been shown and described in connection with the preferred embodiments thereof, it will be understood that many modifications, substitutions, and additions may be made which are within the intended broad scope of the following claims. From the foregoing, it can be seen that the present invention accomplishes at least all of the stated objectives.

What is claimed is:

1. An aortic cannula for supplying blood to the aorta during heart surgery, comprising:

an elongated tube having a longitudinal axis and a terminal end with an opening therein;

a ramped surface adjacent the terminal end to direct the flow of blood from the cannula in a direction approximately 70°–90° to the longitudinal axis, and the terminal end including a substantially flat lip extending from the ramped surface and beyond the perimeter of the tube.

2. The cannula of claim 1 wherein the lip extends approximately 70°–90° relative to the longitudinal axis.

3. The cannula of claim 1 wherein the opening is disposed on the tube to direct blood toward the ascending aorta.

4. The cannula of claim 1 wherein the opening has a substantial width permitting a fanned broadcast of blood from the opening.

5. The cannula of claim 1 wherein the terminal end of the tube is angled with respect to the longitudinal axis.

6. The cannula of claim 5 wherein the angle of the terminal end is approximately 8° to 18° relative to the longitudinal axis.

7. An improved aortic cannula for supplying blood to the aorta during open heart surgery, comprising:

an elongated tube having a longitudinal axis and a terminal end with an opening therein; and wherein the opening having a curved perimeter edge and a substantial width so as to produce a fanned broadcast of blood from the opening.

8. The cannula of claim 7 further comprising a substantially flat lip on the terminal end adjacent the opening and extending approximately 70°–90° relative to the longitudinal axis to direct blood blow from the cannula in a direction substantially 70°–90° to the longitudinal axis.

9. The cannula of claim 8 wherein the lip extends beyond the perimeter of the tube.

10. The cannula of claim 7 further comprising a ramped surface on the terminal end and located upstream from the lip to minimize turbulence of the blood flow as the blood exits the opening of the tube.

11. The cannula of claim 7 wherein the opening is disposed on the tube to direct blood flow toward the ascending aorta.

12. The cannula of claim 7 wherein the terminal end of the tube is angled with respect to the longitudinal axis.

13. The cannula of claim 7 wherein the angle of the terminal end is approximately 8° to 18° relative to the longitudinal axis.

14. The cannula of claim 1 wherein the opening has a non-planar curved perimeter edge.

15. The cannula of claim 14 wherein the opening has opposite sides extending approximately 180° with respect to the perimeter of the tube.

16. The cannula of claim 1 wherein the opening has opposite sides extending approximately 180° with respect to the perimeter of the tube.

17. The cannula of claim 1 wherein the opening has recessed opposite sides.

18. The cannula of claim 1 wherein the opening has an upper portion, and the lip extends substantially beyond the upper portion of the opening.

19. The cannula of claim 7 wherein the opening has opposite sides extending approximately 180° with respect to the perimeter of the tube.

20. The cannula of claim 7 wherein the opening has recessed opposite sides.

21. A method of minimizing stroke or embolism in a patient during open heart surgery, comprising: making an opening in the aorta;

inserting a cannula through the opening, the cannula having a terminal end with an opening therein through which blood is discharged;

orienting the cannula opening so as to be directed toward the ascending aorta, thereby precluding blood flow from the cannula in a direction toward the aortic arch.

22. The method of claim 21 further comprising directing the blood out of the cannula in a direction approximately 70°–90° from the longitudinal axis of the cannula.

23. The method of claim 21 wherein the blood is directed along a ramped surface adjacent the opening at the terminal end of the cannula, the ramped surface changing the blood flow path approximately 70°–90° from the longitudinal axis.

24. The method of claim 21 wherein the blood is directed along a lip adjacent the opening and extending approximately 70°–90° relative to the longitudinal axis.

25. The method of claim 21 wherein the blood is broadcast from the opening in a radius of approximately 90°.

* * * * *